(12) United States Patent
Kohgo et al.

(10) Patent No.: US 8,623,661 B2
(45) Date of Patent: Jan. 7, 2014

(54) IRON CHELATING AGENT, METHOD FOR PRODUCING SAME, METHOD FOR DETERMINING AMOUNT OF IRON IONS AND METHOD FOR TRAPPING IRON IONS

(75) Inventors: Yutaka Kohgo, Asahikawa (JP); Katsuya Ikuta, Asahikawa (JP); Katsunori Sasaki, Asahikawa (JP); Yuzo Nishida, Kanazawa (JP)

(73) Assignees: National University Corporation Asahikawa Medical College, Asahikawa-shi (JP); Yamagata University, Yamagata-shi (JP)

( * ) Notice: Subject to any disclaimer, the term of this patent is extended or adjusted under 35 U.S.C. 154(b) by 58 days.

(21) Appl. No.: 13/120,126

(22) PCT Filed: Sep. 18, 2009

(86) PCT No.: PCT/JP2009/004765
§ 371 (c)(1),
(2), (4) Date: Apr. 25, 2011

(87) PCT Pub. No.: WO2010/032489
PCT Pub. Date: Mar. 25, 2010

(65) Prior Publication Data
US 2011/0189779 A1    Aug. 4, 2011

(30) Foreign Application Priority Data
Sep. 22, 2008 (JP) ................................ 2008-243095

(51) Int. Cl.
*G01N 33/20* (2006.01)
*C07C 229/14* (2006.01)
*C07D 233/64* (2006.01)
*C07C 229/26* (2006.01)

(52) U.S. Cl.
USPC ........... 436/84; 562/444; 562/448; 548/339.1

(58) Field of Classification Search
USPC ................... 436/84; 562/444, 448; 548/339.1
See application file for complete search history.

(56) References Cited

U.S. PATENT DOCUMENTS

| | | | |
|---|---|---|---|
| 4,224,034 A * | 9/1980 | Denney et al. | ................ 436/74 |
| 5,594,012 A | 1/1997 | Kitazawa et al. | |
| 6,218,432 B1 | 4/2001 | Galey et al. | |

FOREIGN PATENT DOCUMENTS

| | | |
|---|---|---|
| EP | 0 629 606 A1 | 12/1994 |
| JP | 2000-506546 | 5/2000 |

(Continued)

OTHER PUBLICATIONS

Bleomycin-detectable Iron Assay for Non-Transferrin-bound Iron in Hematologic Malignancies Leni von Bonsdorff, Inni Lindeberg, Leila Sahlstedt, Jari Lehto, Jaakko Parkkinen Clinical Chemistry 48:2 307-314, 2002.*

(Continued)

*Primary Examiner* — Krishnan S Menon
*Assistant Examiner* — Dwan A Gerido
(74) *Attorney, Agent, or Firm* — Knobbe Martens Olson & Bear LLP (57) ABSTRACT

The present invention provides an iron chelating agent which can selectively chelate iron ions. The iron chelating agent of the present invention includes a compound represented by the following formula (1) or a salt thereof (wherein, ring Z represents an aromatic hydrocarbon ring or an aromatic heterocyclic ring; $R^1$ represents an alkylene group; $R^2$ and $R^3$ each independently represent a hydrogen atom, a hydrocarbon group or a group having chelating ability; and the total coordination number of the groups represented by $R^2$ and $R^3$ is 1 or 2.)

14 Claims, 2 Drawing Sheets

(56) References Cited

FOREIGN PATENT DOCUMENTS

| | | |
|---|---|---|
| JP | 2000-507601 | 6/2000 |
| JP | 2002-502816 | 1/2002 |
| JP | 2002-173473 A | 6/2002 |
| JP | 2004-203820 | 7/2004 |
| JP | 2005-509649 | 4/2005 |
| JP | 2006-504748 | 2/2006 |
| JP | 2007-532509 | 11/2007 |
| JP | 2008-520669 | 6/2008 |
| WO | WO 97/49395 | 12/1997 |
| WO | WO 99/39706 | 8/1999 |
| WO | WO 03/039541 | 5/2003 |
| WO | WO 2004/035026 | 4/2004 |
| WO | WO 2005/097062 | 10/2005 |
| WO | WO 2006/055412 | 5/2006 |

OTHER PUBLICATIONS

European Search Report issued in 09814334.0 on Jan. 20, 2012.
Alam et al.; "Structural Characterization of an Enantiopure Hydroxo-Bridged Binuclear Iron(III) Complex with Empty One-Dimensional Helical Channels;" Inorganic Chemistry, vol. 44, No. 5, pp. 1302-1308, Mar. 2, 2005.
Shah, Sudhir V.; "Oxidants and Iron in Chronic Kidney Disease;" Kidney International, Supplement 200410 US, vol. 66, No. 91, pp. S50-S55, Oct. 2004.
Ozawa et al., *Polyhedron* (1994), 13 (15): 2343-2351.
Kitazawa, et al., *Biochimica et Biophysica Acta* (1999) 1473: 400-408.
Tyrrell, et al., *Free Radical Biology & Medicine*, (2002) 33 (3): 356-363.
Faller, et al. *J. Med Chem.* (2000) 43: 1467-1475.
Martell, et al., *Inorganica Chimica Acta* (1999) 291:238-246.
Chua, et al. *Eur. J. Biochem* (2003) 270:1689-1698.
Pakhomova, et al. *Collect. Czech. Chem. Commun*, (1997) 62:1205-1213.
Ma, et al., *Inorganic Chemistry Communications* (Dec. 4, 2007) 11:256-259.
Shongwe, et al., *J. Chem Soc.*, Dalton Trans. (2002) 4064-4069.
International Search Report issued in corresponding PCT Application No. PCT/JP2009/004765, mailed Oct. 27, 2009.

* cited by examiner

IRON CHELATING AGENT, METHOD FOR PRODUCING SAME, METHOD FOR DETERMINING AMOUNT OF IRON IONS AND METHOD FOR TRAPPING IRON IONS

RELATED APPLICATIONS

This application is the U.S. National Phase filing under 35 U.S.C. §371 of PCT/JP2009/004765, filed Sep. 18, 2009, which designated the United States and was published in a language other than English, which claims priority under 35 U.S.C. §119(a)-(d) to Japanese Patent Application No. 2008-243095, filed Sep. 22, 2008. The contents of these applications are incorporated herein by reference in their entireties.

TECHNICAL FIELD

The present invention relates to an iron chelating agent, for example, an iron chelating agent capable of chelating non-transferrin-bound iron, a method for determining the amount of iron ions and a method for trapping iron ions.

BACKGROUND ART

Recently, a new disease concept called Chronic Kidney Disease (CKD) has been identified and has attracted worldwide attention. Chronic Kidney Disease is treated by the use of angiotensin II inhibitors, by diet control by means of rice with low protein content, and by the control of various risk factors. However, 40,000 people undergo dialysis annually, which carries a risk of death as a consequence of cardiovascular disturbance complications, and accordingly there is a demand for a new treatment method. As a treatment method for chronic kidney disease, a method of removing non-transferrin-bound iron (NTBI), and a carbonyl compound that are the main causes of chronic kidney disease is effective.

As a treatment methods of removing iron from a living body (in particular, non-transferrin-bound iron (NTBI)), there are (1) phlebotomy, (2) an iron-limiting diet, (3) medical therapy using an iron chelating agent, and (4) extracorporeal circulating and cleaning therapy. Phlebotomy is good in terms of patient Quality of Life (QOL), but results in side effects such as anemia or hypoproteinemia and can only be applied to patients who do not suffer from anemia. The iron-limiting diet results in side effects such as nutrition imbalance and can only be applied to some hepatic diseases. The medical therapy using an iron chelating agent has a pronounced iron chelating effect and is mainly used with patients who have an iron overload disorder after a blood transfusion. However, it is said that in iron-related organ disorders resulting from a mild iron overload disorder or an iron metabolism disorder, side effects caused by over-chelating occur with high frequency. Further, extracorporeal circulating and cleaning therapy is a method of removing iron (iron ions) by extracorporeal circulation of blood and has a property of enabling the treatment of unstable iron having toxicity in a living body without causing organ toxicity by over-chelating.

As a result, a method of removing non-transferrin-bound iron by extracorporeal circulation and cleaning therapy has been studied. There is a demand for the development of a ligand (iron chelating agent) which specifically and effectively adsorbs non-transferrin-bound iron. In particular, there is a demand for the development of an iron chelating agent capable of trapping only non-transferrin-bound iron without having chelating ability with respect to transferrin-bound iron which is useful for a living body (that is, without trapping transferrin-bound iron).

Further, when chronic kidney disease enters stage 4, load is applied on the remaining nephrons due to the increased number of failed nephrons and thus more nephrons fail; dialysis must be introduced as a result of falling into this vicious circle. On the other hand, in stage 3, the risk of cardiovascular pathology is markedly increased. The dialysis treatment needs be carried out three times per week, and the time required to perform the dialysis is 4 hours and thus the QOL of a patient is decreased, as well as causing the loss of the chance to work. Therefore, as long as treatment is carried out in stage 3, introduction of dialysis and cardiovascular disturbance complications can be prevented, which can lead to a reduction in high medical expenses (it is said that dialysis expenses may exceed 1.2 trillion yen in Japan).

Meanwhile, various proposals have been made in regard to an iron chelating agent capable of chelating iron ions (for example, see Patent Literature 1 to 8).

Further, there is a problem in that, in a method of determining the amount of non-transferrin-bound iron using high-performance liquid chromatography, NTBI values in the blood of healthy persons are often represented as negative values and this leads to a lack of reliability. It is thought that, by clarifying and ameliorating the problems of the NTBI measuring system using HPLC, a stable and highly sensitive NTBI measuring system could be constructed and that, as a result, NTBI values in the blood of healthy persons could be precisely determined.

PATENT LITERATURE

[PTL 1] PCT Japanese Translation Patent Publication No. 2007-532509
[PTL 2] PCT Japanese Translation Patent Publication No. 2006-504748
[PTL 3] PCT Japanese Translation Patent Publication No. 2005-509649
[PTL 4] PCT Japanese Translation Patent Publication No. 2000-507601
[PTL 5] PCT Japanese Translation Patent Publication No. 2008-520669
[PTL 6] PCT Japanese Translation Patent Publication No. 2002-502816
[PTL 7] PCT Japanese Translation Patent Publication No. 2000-506546
[PTL 8] Japanese Unexamined Patent Application Publication No. 2004-203820

SUMMARY OF INVENTION

Technical Problem

The present invention provides an iron chelating agent capable of selectively chelating iron ions, in particular, non-transferrin-bound iron, and a production method thereof. Further, the present invention provides a method of determining the amount of iron ions using the iron chelating agent of the present invention and a method of trapping iron ions using the iron chelating agent of the present invention. Further, the present invention provides a stable and highly sensitive NTBI measuring system.

Solution to Problem

The inventors carried out intensive studies to achieve the objects, and as a result, found that a phenol-based chelating agent having a structure where a specific amino acid is introduced is capable of selectively chelating iron ions, whereby iron ions such as non-transferrin-bound iron can be effectively determined in its amount and trapped. They also found that by removing iron ions of reagents or solvents used in the pretreatment of samples using a chelating agent or an ion exchange resin, or by employing a subtraction method removing a background, a stable and a highly sensitive NTBI measuring system can be provided, thus completing the present invention.

That is, the present invention is

[1] An iron chelating agent, having chelating ability with iron ions, wherein the chelating agent is a compound represented by the following formula (1) or a salt thereof.

[chem. 1]

(1)

(wherein, ring Z represents an aromatic hydrocarbon ring or an aromatic heterocyclic ring. $R^1$ represents an alkylene group. $R^2$ and $R^3$ each independently represent a hydrogen atom, a hydrocarbon group or a group having chelating ability, and the sum of coordination number of groups represented by $R^2$ and $R^3$ is 1 or 2.)

[2] The iron chelating agent according to [1], wherein the ring Z in formula (1) is a six-membered aromatic hydrocarbon ring or an aromatic heterocyclic ring.

[3] The iron chelating agent according to [2], wherein the ring Z in formula (1) is a benzene ring.

[4] The iron chelating agent according to any one of [1] to [3], wherein $R^1$ in formula (1) is a methylene group.

[5] The iron chelating agent according to any one of [1] to [4], wherein an $R^2$ group having chelating ability in formula (1) has one or two functional groups selected from a hydroxyl group, a carboxyl group, a carbamoyl group, an amino group, a guanidino group, an amidino group, and a nitrogen atom-containing heterocyclic group.

[6] The iron chelating agent according to [5], wherein an $R^2$ group having chelating ability in formula (1) is a carboxyalkyl group, a hydroxyalkyl group, a carbamoylalkyl group, a pyridylalkyl group, a pyrazinylalkyl group, a pyrimidinylalkyl group, a pyrrolylalkyl group, an imidazolylalkyl group, a benzoimidazolylalkyl group or a pyrazolylalkyl group.

[7] The iron chelating agent according to any one of [1] to [6], wherein an $R^3$ group having chelating ability in formula (1) is a hydroxymethyl group, a 1-hydroxyethyl group, (p-hydroxyphenyl)methyl group, an indolylmethyl group, a carbamoylmethyl group, a 2-carbamoylethyl group, a carboxymethyl group, a 2-carboxyethyl group, a 4-aminobutyl group, a (1H-imidazol-4-yl)methyl group, a 3-guanidinopropyl group, a mercaptomethyl group or a 2-methylthioethyl group, a hydrocarbon group of $R^3$ is a methyl group, a 1-methylethyl group, a 2-methylpropyl group, 1-methylpropyl group or a phenylmethyl group.

[8] The iron chelating agent according to [7], wherein $R^3$ in formula (1) is a hydroxymethyl group, a 1-hydroxyethyl group, a (p-hydroxyphenyl)methyl group, an indolylmethyl group, a carbamoylmethyl group, a 2-carbamoylethyl group, a carboxymethyl group, a 2-carboxyethyl group, a 4-aminobutyl group, a (1H-imidazol-4-yl)methyl group or a 3-guanidinopropyl group, and $R^2$ in formula (1) is a hydrogen atom.

[9] The iron chelating agent according to [7], wherein $R^3$ in formula (1) is a methyl group, a 1-methylethyl group, a 2-methylpropyl group, a 1-methylpropyl group, or a phenylmethyl group, and $R^2$ in formula (1) is a group having chelating ability.

[10] The iron chelating agent according to any one of [1] to [9], wherein ring Z and $R^1$ to $R^3$ in formula (1) do not contain a sulfur atom.

[11] The iron chelating agent according to any one of [1] to [10], wherein the agent is a four or five-coordinated ligand.

[12] The iron chelating agent according to any one of [1] to [11], wherein the agent has chelating ability with respect to non-transferrin-bound iron.

[13] A method of producing the iron chelating agent according to any one of [1] to [12], including a step of reacting an aromatic compound or a heterocyclic compound having a structure where a hydroxyl group and a formyl group or a formylalkyl group are bonded to adjacent carbon atoms, with an amino acid or a salt thereof corresponding to an amino acid residue in formula (1).

[14] The producing method according to [13], wherein the amino acid corresponding to the amino acid residue in formula (1) is serine, threonine, tyrosine, tryptophan, asparagine, glutamine, aspartic acid, glutamic acid, lysine, histidine, or arginine.

[15] A method of determining an amount of iron ions by using the iron chelating agent according to any one of [1] to [12].

[16] The method of determining an amount of iron ions according to [15], which determines the amount by absorption spectrometry.

[17] The method of determining an amount of iron ions according to [15] or [16], wherein the iron ions are non-transferrin-bound iron.

[18] The method of determining an amount of iron ions according to any one of [15] to [17], further including a step of removing iron from reagents, equipment, and/or solvents used in the determination of an amount.

[19] The method of determining an amount of iron ions according to [18], wherein the iron removal is carried out by a chelating agent.

[20] The method of determining an amount of iron ions according to any one of [15] to [19], wherein two parts are taken from samples for which the amount is to be determined, one part is used as a sample for measuring the total concentration of iron, the other part is used as a sample for measuring the concentration of iron not originating from the samples for which the amount is to be determined, and the iron concentration not originating from samples for which the amount is to be determined is subtracted from the total iron concentration to determine the true iron concentration.

[21] A method of trapping iron ions using the iron chelating agent according to any one of [1] to [12].

The method of trapping iron ions according to [21], wherein the iron ions are non-transferrin-bound iron.

Advantaegous Effects of Invention

The iron chelating agent of the present invention is capable of selectively chelating iron ions, in particular, effectively chelating non-transferrin-bound iron.

DESCRIPTION OF EMBODIMENTS

[Iron Chelating Agent]

The iron chelating agent of the present invention is a compound represented by formula (1). The compound represented by formula (1) bonds a hydroxyl group (—OH group) and an amino acid residue-alkylene group (—$R^1$—$NR^2$—$CHR^3$—COOH group) to adjacent carbon atoms in ring Z. In other words, the iron chelating agent of the present invention has a structure (tripod type) where a hydroxyl group and an amino acid residue-alkylene group are bonded to carbon atoms of ring Z in a position relationship at the ortho position.

For example, the inventors of the present invention carried out various studies in which the chelating agent of Patent Document 1 also had a predetermined structure (a tripod type structure) at the ortho position to a hydroxyl group of phenol, and as a result, the inventors found that the chelating agent according to the present invention bonds the predetermined substituent containing an amino acid residue-alkylene group at the ortho position to the hydroxyl group, and thereby can selectively trap only non-transferrin-bound iron without trapping transferrin-bound iron.

As for the chelating agent according to the present invention, a substituent at the ortho position to a hydroxyl group of a phenol-based chelating agent has a (—$R^1$—$NR^2$—$CHR^3$—COOH) structure and the number of coordinated atoms coordinatable to iron ions in the substituent is 3 to 4. The inventors found that non-transferrin-bound iron can be selectively trapped in the phenol-based chelating agent and that when the coordination number in the substituent at the ortho position to a hydroxyl group is 3 to 4, selectivity can be increased at the time when the iron ions combine with a coordinatable hydroxyl group and trap the non-transferrin-bound iron. In other words, the iron chelating agent of the present invention is a four-coordinated ligand that has a total coordination number of 4 or a five-coordinated ligand that has a total coordination number of 5.

In the substituent, N of an amino acid residue and O of a carboxyl group are coordinated atoms of iron ions and one or two coordinated atoms are suitably provided in a group represented by $R^2$ and $R^3$ in the substituent. Therefore, a chelating agent that selectively traps non-transferrin-bound iron can be provided.

When the group represented by $R^2$ and $R^3$, as described above, is a combination with a total coordination number of 1 to 2, it can be suitably selected and used from a group consisting of a hydrogen atom, hydrocarbon and a group having chelating ability.

As the group containing $R^2$, it is preferable that an amino acid residue containing N is used, whereby N becomes a preferable coordinated atom in relation to iron ions. Further, by selecting, as the amino acid residue, one corresponding to an amino acid forming protein in a living body, toxicity generated upon application to the human body can be suppressed to be extremely low. Therefore, a chelating agent having extremely high safety in respect to the human body can be provided. Further, as a group represented by $R^1$, an alkylene group having no coordinated atom for iron ions is preferably used. At this time, when the alkylene group has approximately 1 to 10 carbon atoms, non-transferrin-bound iron can be selectively chelated. As for the size of an alkylene group represented by $R^1$, it has been clarified by the studies of the present inventors that in particular the nitrogen of the amino acid residue connected to R1 affects the degree of coordinated force shown with respect to iron ions. In particular, in order to increase the selectivity of non-transferrin-bound iron, it is preferable to have approximately 1 to 4 carbon atoms, in particular, the selectivity of non-transferrin-bound iron can be increased by using a methylene group.

According to the chelating agent of the present invention which is formed as described above, by disposing a suitable number of coordinated atoms at suitable positions in the chelating agent for trapping non-transferrin-bound iron, the non-transferrin-bound iron can be selectively trapped, and, alongside this, the chelating agent is disposed so as to enclose the iron ions, whereby a stable complex is formed and further dissociation of the iron ions can be prevented.

When a substituent and a hydroxyl group can be supported at suitable positions in a phenol-based chelating agent where the substituent is bonded, ring Z forming a phenol portion in formula (1) may be any one of an aromatic hydrocarbon ring or an aromatic heterocyclic ring, but an aromatic hydrocarbon ring is more preferable.

The ring Z is preferably a five- or more-membered ring, more preferably a five-to eight-membered ring and particularly preferably a six-membered ring. In other words, a six-membered aromatic hydrocarbon ring (benzene ring) is most preferable as the ring Z. Further, it is preferable that the aromatic heterocyclic ring of ring Z contains at least two atoms selected from a carbon atom, a nitrogen atom, and an oxygen atom as atoms forming the ring (ring-forming atoms). It is most preferable that the ring contains only a carbon atom and a nitrogen atom. Examples of an aromatic heterocyclic ring containing only a carbon atom and a nitrogen atom as the ring-forming atom include a six-membered aromatic heterocyclic ring such as a pyridine ring, a pyridazine ring, pyrimidine ring, and a pyrazine ring.

The aromatic hydrocarbon ring and aromatic heterocyclic ring as ring Z may have a substituent. In other words, a substituent may be bonded to a ring-forming atom other than the carbon atom where a hydroxyl group or an amino acid residue-alkylene group is bonded. Substituents may form a ring [an aromatic ring (aromatic hydrocarbon ring or aromatic heterocyclic ring, or the like), a non-aromatic ring (non-aromatic hydrocarbon ring or non-aromatic heterocyclic ring, or the like) or the like] by bonding with each other. The substituent is not specifically limited as long as the substituent is a group that does not inhibit the chelating ability by a hydroxyl group or an amino acid residue-alkylene group. For example, when ring Z is a benzene ring, the substituent is preferably 5-Cl or 3-OH or the like. Further, the substituent is preferably a group having no chelating ability. Specifically, the substituent may be a hydrocarbon group such as an alkyl group.

Examples of the alkylene group of $R^1$ include an alkylene group having 1 to 10 carbon atoms such as a methylene group, an ethylene group, a trimethylene group, a propylene group, or a tetramethylene group, and an alkylene group having 1 to 4 carbon atoms is preferable. Specifically, a methylene group or an ethylene group is preferable, and a methylene group is most preferable.

$R^2$ and $R^3$ each independently represent a hydrogen atom, a hydrocarbon group or a group having chelating ability.

The hydrocarbon group of $R^2$ and $R^3$ is a group having no chelating ability, and for example, includes an alkyl group, an aryl group, an aralkyl group, and a cycloalkyl group. Examples of the alkyl group include a straight and branched alkyl group such as a methyl group, an ethyl group, a propyl group, an isopropyl group, a butyl group, an isobutyl group, an s-butyl group, a t-butyl group, a pentyl group, a hexyl group, a heptyl group, and an octyl group. Examples of the aryl group include a phenyl group and a naphthyl group. Examples of the aralkyl group include a phenylmethyl group. Examples of the cycloalkyl group include a cyclohexyl group, a cycloheptyl group, and a cyclooctyl group.

The hydrocarbon group of $R^3$ preferably includes a methyl group ("—$CH_3$"), a 1-methylethyl group ("—$CH(CH_3)CH_3$"), a 2-methylpropyl group ("—$CH_2CH(CH_3)CH_3$"), a 1-methylpropyl group ("—$CH(CH_3)CH_2CH_3$") or a phenylmethyl group ("a group represented by the following formula (2a)"), corresponding to an amino acid forming protein in a living body.

Examples of the group having chelating ability in $R^2$ include a group having a functional group such as a hydroxyl group, a carboxyl group, a carbamoyl group, an amino group, a guanidino group, an amidino group, and a nitrogen atom-containing heterocyclic group; preferably a group having one or two functional groups selected from a hydroxyl group, a carboxyl group, a carbamoyl group and a nitrogen atom-containing heterocyclic group; more preferably an alkyl group having one or two functional groups selected from a hydroxyl group, a carboxyl group, a carbamoyl group, and a nitrogen atom-containing heterocyclic group. Examples of the alkyl group include a straight and branched alkyl group such as a methyl group, an ethyl group, a propyl group, an isopropyl group, a butyl group, an isobutyl group, an s-butyl group, a t-butyl group, a pentyl group, a hexyl group, a heptyl group, or an octyl group. Specific examples of the group include a carboxyalkyl group, a hydroxyalkyl group, a carbamoylalkyl group, a pyridylalkyl group, a pyrazinylalkyl group, a pyrimidinylalkyl group, a pyrrolylalkyl group, an imidazolylalkyl group, a benzoimidazolylalkyl group, or a pyrazolylalkyl group. Examples of the nitrogen atom-containing heterocyclic ring include an aromatic heterocyclic ring such as a pyridine ring, a pyridazine ring, a pyrimidine ring, a pyrazine ring, a pyrrole ring, an imidazole ring, a benzoimidazole ring, a pyrazole ring, a furan ring, an oxazole ring, and an isoxazole ring.

The group having chelating ability in $R^3$ may be the same group as one having chelating ability in $R^2$, and preferably includes a hydroxymethyl group ("—$CH_2OH$"), a 1-hydroxyethyl group ("—$CH(OH)CH_3$"), a (p-hydroxyphenyl)methyl group ("a group represented by the following formula (2b)"), an indolylmethyl group ("a group represented by the following formula (2c)"), a carbamoylmethyl group ("—$CH_2CONH_2$"), a 2-carbamoylethyl group ("—$CH_2CH_2CONH_2$"), a carboxymethyl group ("—$CH_2COOH$"), a 2-carboxyethyl group ("—$CH_2CH_2COOH$"), a 4-aminobutyl group ("—$CH_2CH_2CH_2CH_2NH_2$"), a (1H-imidazol-4-yl)methyl group ("a group represented by the following formula (2d)"), a 3-guanidinopropyl group ("—$CH_2CH_2CH_2NHC(\!\!=\!\!NH)NH_2$"), a mercaptomethyl group ("—$CH_2SH$") or a 2-methylthioethyl group ("—$CH_2CH_2SCH_3$"), corresponding to an amino acid forming protein in a living body. Therefore, the iron chelating agent of the present invention has a structure where a harmless amino acid is introduced to the human body, and thus has extremely high safety with respect to the human body.

[Chem. 2]

(2a)

(2b)

(2c)

(2d)

In the present invention, it is critical that the sum of the coordination numbers (actual coordination number coordinated to iron ions) of groups represented by $R^2$ and $R^3$ is 1 or 2. In other words, according to the description based on $R^3$, when $R^3$ is a group (hydrogen atom or hydrocarbon group) having no chelating ability, $R^2$ is a group having chelating ability with a coordination number of 1 or 2. When $R^3$ is a group having chelating ability with a coordination number of 1, $R^2$ is a group having no chelating ability or a group having chelating ability with a coordination number of 1. When $R^3$ is a group having chelating ability with a coordination number of 2, $R^2$ is a group having no chelating ability. For example, in a case where an amino acid forming protein in a living body is used as the material, when a group corresponding to $R^3$ has chelating ability, $R^2$ is an unchanged hydrogen atom and there is no need to introduce other groups, and, when $R^3$ is a group having no chelating ability, a group having chelating ability needs to be introduced as $R^2$.

Specifically, when $R^3$ is a group having chelating ability such as a hydroxymethyl group, a 1-hydroxyethyl group, a (p-hydroxyphenyl)methyl group, an indolylmethyl group, a carbamoylmethyl group, a 2-carbamoylethyl group, a carboxymethyl group, a 2-carboxyethyl group, a 4-aminobutyl group, a (1H-imidazol-4-yl)methyl group, or a 3-guanidinopropyl group, $R^2$ is a hydrogen atom or a hydrocarbon group having no chelating ability, and is preferably a hydrogen atom.

When $R^3$ is a group having no chelating ability such as a hydrogen atom, a methyl group, a 1-methylethyl group, a 2-methylpropyl group, a 1-methylpropyl group, or a phenylmethyl group, $R^2$ is a group having chelating ability. Specifically, $R^2$ preferably includes a chelating group having a coordination number of one (coordination number of actually coordinated atoms) such as a carboxyalkyl group, a hydroxyalkyl group, a carbamoylalkyl group, a pyridylalkyl group, a pyrazinylalkyl group, a pyrimidinylalkyl group, a pyrrolylalkyl group, an imidazolylalkyl group, a benzoimidazolylalkyl group, and a pyrazolylalkyl group.

It is preferable that ring Z and $R^1$ to $R^3$ in the iron chelating agent of the present invention do not contain a sulfur atom. The sulfur atom in the chelating agent has high affinity with respect to metal ions other than iron ions. Therefore, there is a concern that the inclusion of a sulfur atom in some portion of the chelating agent will result in a reduction of selectivity to non-transferrin-bound iron.

The iron chelating agent of the present invention is a compound represented by formula (1) or a salt thereof. Examples of the salt forms include alkali metal salts such as a sodium salt or a potassium salt, or an ammonium salt of the compound represented by formula (1). Further, when the iron chelating agent of the present invention has a salt form, generally, a phenolic hydroxyl group becomes a salt form, but other portions may become a salt form.

Further, the iron chelating agent of the present invention may take the form of a hydrate or solvate. Further, stereoisomers such as optical isomers may be present in the iron chelating agent of the present invention in some cases. When stereoisomers are present in the iron chelating agent, the iron chelating agent may be any stereoisomers, a mixture of any stereoisomers or take a racemic form.

The various functional groups of the iron chelating agent of the present invention, such as a hydroxyl group or a carboxyl group, may be protected by a protective group during the period before the chelating agent is used. However, it is critical that such protective groups are removed when the iron chelating agent is used and the various functional groups such as the hydroxyl group or the carboxyl group are restored to a separate state.

The iron chelating agent of the present invention has four-coordinated ligands of which the coordination number is four or five-coordinated ligands of which the coordination number is five. Further, the iron chelating agent of the present invention has a structure where a hydroxyl group and an amino acid residue-alkylene group are bonded to adjacent carbon atoms in ring Z. That is to say, the chelating agent has a structure (tripod type) where the amino acid residue-alkylene group is bonded at the ortho position to a hydroxyl group bonded to a carbon atom of ring Z.

The iron chelating agent of the present invention has four- or five-coordinated ligands and is a tripod type, and one iron chelating agent can be coordinated to one iron ion. That is to say, the iron chelating agent of the present invention has a mononuclear coordination (complex) form where one iron chelating agent is coordinated to one iron ion, and can be coordinated to the iron ion. Therefore, the iron ions are encapsulated in a complex coordinated to the iron ion by the iron chelating agent of the present invention and are not easily dissociated (not moved). Therefore, when the iron chelating agent is applied to the human body, the toxicity to the human body (particularly the kidney) is extremely low, and thus safety with regard to the human body is extremely high. Further, since the iron chelating agent of the present invention can form that portion of amino acid residue forming the protein of a living body, such as serine, histidine, or glutamine, the toxicity to the human body is extremely low and thus safety with regard to the human body is extremely high.

Further, iron ions chelatable by the iron chelate of the present invention may be any iron ions, further the valency of the iron ion may be any one of divalency and trivalency, and is preferably trivalency. Further, the iron ions may be non-transferrin-bound iron, since all non-transferrin-bound iron is trivalent iron ion.

In the present invention, non-transferrin-bound iron means an iron ion which is not bonded to transferrin and is capable of having an adverse effect on the human body. Therefore, for example, the non-transferrin-bound iron does not include iron bonded to transferrin (iron ion in transferrin iron complex; transferrin-bound iron); iron stored in the liver, spleen, and marrow as ferritin; hemoglobin formed of four molecules of heme (porphyrin complex compound having iron) and one molecule of globin (four polypeptide chains) in red blood cells; or myoglobin containing one heme which is present in muscle and is a color protein where oxygen molecules are stored until they are needed for metabolism. It is thought that iron ions such as a non-transferrin-bound iron do not have a completely dissociated form in a living body, and take the form of a pair of an iron ion and an anion. Examples of the anion include a hydroxy ion (OH—), or the like. That is to say, it is considered that non-transferrin-bound iron exists in a form such as $Fe^{3+}.3(OH^-)$ or a hydroxy-citrate- (Cit) complex $(FeCitOH^-)$ in a living body.

The iron chelating agent of the present invention can be used for the medical application described above. For example, when the iron chelating agent is administrated to a human body, it can be orally or parenterally administered. Examples of the parenteral administration include intravenous, intramuscular, interadermal, or subcutaneous injection. Further, the iron chelating agent can be used in industrial applications other than medical applications.

[Production Method of Iron Chelating Agent]

Any production method may be used as the method of producing the iron chelating agent of the present invention, as long as the method is one which can produce the iron chelating agent of the present invention represented by formula (1). For example, there is a preferable production method including a step of reacting an aromatic hydrocarbon ring compound or an aromatic heterocyclic ring compound having a structure where a hydroxyl group and a formyl group or a formylalkyl group are bonded to adjacent carbon atoms, with an amino acid or a salt thereof corresponding to an amino acid residue in formula (1). According to this method, the iron chelating agent of the present invention can be efficiently produced with mild conditions and at low cost.

In formula (1), when the iron chelating agent where ring Z is a benzene ring and $R^1$ is a methylene group is produced, salicylaldehyde can be used as a substance (aromatic hydrocarbon ring compound or aromatic heterocyclic ring compound having a structure where a hydroxyl group and a formyl group or a formylalkyl group are bonded to adjacent carbon atoms).

Further, examples of the amino acid corresponding to the amino acid residue in formula (1) which can be used include glycine, alanine, valine, leucine, isoleucine, phenylalanine, serine, threonine, tyrosine, tryptophan, asparagine, glutamine, aspartic acid, glutamic acid, lysine, histidine, arginine, cysteine, and methionine, which are amino acids forming protein in a living body. Among them, the amino acids which may be preferably applied include serine, threonine, tyrosine, tryptophan, asparagine, glutamine, aspartic acid, glutamic acid, lysine, histidine, arginine, cysteine, and methionine, which include a group having chelating ability at the position corresponding to $R^3$. In particular, the amino acids having no sulfur atom which are preferably used include serine, threonine, tyrosine, tryptophan, asparagine, glutamine, aspartic acid, glutamic acid, lysine, histidine, arginine. That is to say, an amino acid having a group having chelating ability can be used, and thereby the iron chelating agent of the present invention can be simply produced without the need to introduce a group having separate chelating ability. Further, the iron chelating agent produced by using the amino acid forming protein in a living body has extremely high safety in respect to the human body. It is suitably substituted and used by adding and deleting a functional group of a group corresponding to $R^3$ of the amino acid.

For example, in formula (1), when the iron chelating agent where ring Z is a benzene ring and $R^1$ is a methylene group, $R^2$ is a hydrogen atom, and $R^3$ is a hydroxymethyl group (amino acid residue is serine residue) is produced, an iron chelating agent can be produced by the production method having a step of reacting salicylaldehyde and serine or a salt thereof.

More specifically, for example, aqueous sodium hydroxide solution (2N aqueous sodium hydroxide solution) is added to a beaker, D,L-serine (powder) is added as it is by little and little under stirring at room temperature (about 10 to 30° C.), followed by stirring for 30 minutes, thereby dissolving serine in aqueous sodium hydroxide solution. Subsequently, water is removed using an evaporator at a temperature of 40 to 50° C. The white residue is added to methanol using a beaker while being stirred at room temperature (about 10 to 30° C.), and then be stirred for 30 minutes. The resultant is dissolved and salicylaldehyde having the same number of moles as D,L-serine is directly added to this solution at room temperature (about 10 to 30° C.) while being stirred. At this time, the solution rapidly becomes a yellow color. Methanol is completely removed by an evaporator at the temperature of 30 to 40° C., the remaining yellow solid is dissolved in methanol in a beaker at room temperature (about 10 to 30° C.) while being stirred. Solid state of sodium borohydride ($NaBH_4$) is added as it is bit by bit to the methanol solution while being stirred at room temperature (about 10 to 30° C.). At this time, the solution becomes white. When all of the yellow components are come out (about 60 minutes), the addition of sodium borohydride is stopped, followed by stirring at room temperature (about 10 to 30° C.) for one hour, a small amount of water is added thereto at room temperature (about 10 to 30° C.), and then insoluble materials are filtered off by natural filtration. Then, the solvent from the filtrate is removed using an evaporator at a temperature of 40 to 50° C., the remaining white residue is added bit by bit to water in a beaker at room temperature (about 10 to 30° C.) while stirring, followed by dissolution in water, and aqueous hydrochloric acid solution (2N aqueous hydrochloric acid solution) is slowly added to this aqueous solution at room temperature (about 10 to 30° C.) while stirring. White crystals are precipitated according to the reduction of the pH of the solution (at this time, the pH is adjusted not to be 1 or lower). Then, the resultant is left (still standing) at room temperature (about 10 to 30° C.) and the crystal is filtered by suction filtration, washed with methanol and dried using a desiccator for 24 hours. The iron chelating agent of the present invention where ring Z is a benzene ring, $R^1$ is a methylene group, $R^2$ is a hydrogen atom, and $R^3$ is a hydroxymethyl group in formula (1) is obtained. Other iron chelating agents can be produced based on this specific production method.

As described above, a reaction of an aromatic hydrocarbon ring compound or an aromatic heterocyclic ring compound having a structure where a hydroxyl group and a formyl group or a formylalkyl group are bonded to adjacent carbon atoms, with an amino acid or a salt thereof corresponding to an amino acid residue in formula (1) can be carried out at room temperature (about 10 to 30° C.), also the reaction can be carried out under very mild conditions. Further, the reaction time in the respective steps is generally within 1 hour and thus the reaction can be carried out rapidly. Furthermore, the reaction can proceed in an air atmosphere, and there is no need for substitution with inert gas (nitrogen gas or the like). Further, aqueous solvents or hydrophilic organic solvents can be used as the solvents. In addition, methanol as a hydrophilic organic solvent can be reused by recovery, and thus it is advantageous from the viewpoint of the environment. Furthermore, the raw materials or the like are relatively inexpensive and thus it is advantageous from the viewpoint of cost. Further, according to the production method, an iron chelating agent having a yield of 50% or more and a purity of approximately 100% can be obtained.

Further, the introduction of a desirable group to $R^2$ is carried out before or after reaction with a substance on the ring Z side, and is preferably carried out after reaction with the substance of the ring Z side from the viewpoint of synthesis. That is to say, the production method having steps A and B described below can be used.

Step A: a step of reacting an aromatic hydrocarbon ring compound or an aromatic heterocyclic ring compound having a structure where a hydroxyl group and a formyl group or formylalkyl group are bonded to adjacent carbon atoms, with an amino acid or a salt thereof corresponding to an amino acid residue in formula (1)

Step B: a step of reacting a compound corresponding to $R^2$ with the chelating agent obtained by step A

[Method of Determining the Amount of Iron Ion]

The method of determining the amount of iron ions of the present invention is characterized by determining the amount of the iron ions using the iron chelating agent of the present invention. The determining method of the present invention can efficiently determine even non-transferrin-bound iron as iron ions. Therefore, for example, the amount of non-transferrin-bound iron in the blood collected from a living body may be determined, and an iron excess state or the like in a living body can be evaluated.

A complex (iron complex or iron chelating form) in which the iron chelating agent of the present invention is coordinated to an iron ion has a characteristic absorption wavelength which is different from the absorption wavelength of iron ions or the iron chelating agent. Therefore, light (for example, light having a wavelength of 466 nm (visible light)) of a desirable wavelength according to the light absorption wavelength of the iron complex is used, allowing absorption spectrometry to be carried out. In addition, since the absorbance of the iron complex depends on the concentration of the iron complex, and absorption strength increases in proportion to the increase in the concentration of the iron complex, the determination of the amount of iron ions can thus be carried out by absorption spectrometry (absorptiometry).

Specifically, according to the method of determining the amount of the iron ions of the present invention, for example, the amount of iron complex (that is to say, the amount of iron ions) can be measured by adding the iron chelating agent solution of the present invention to a solution containing iron ions, and, after reaction (chelating reaction) completion, radiating light (for example, light having a wavelength of 466 nm) of a specific wavelength using a spectrophotometer, whereby an absorbed amount is measured when the light passes through samples (that is to say, solution containing the iron complex). Further, when the amount of iron ions is determined, in advance, the relationship between the absorbance of the iron complex and the concentration of the iron complex is ascertained and calibration data is obtained.

Solvents used for iron ion-containing solutions or iron chelating agent solutions include Dulbecco's phosphate buffered saline (D-PBS), pure water (for example, pure water and the like produced by an ultrapure water producing device (Milli-Q) manufactured by MILLIPORE Corporation; commonly known as Milli-Q water) and the like, when the amount of iron ions is determined. The solvent may be used singly or in combination of two or more kinds.

Further, when an amount of iron ions is determined, the iron chelating agent is added in excess with respect to the number of moles of iron ions, thus it is critical to reliably chelate all the iron ions from the viewpoint of accurately determining the amount of iron ions.

Further, the method of determining the amount of the iron ions of the present invention can be used in medical applications or in industrial applications.

[Trapping Method of Iron Ions]

The trapping method of iron ions of the present invention is characterized by trapping iron ions by using the iron chelating agent of the present invention. The iron chelating agent of the present invention has an extremely high chelating ability in respect to iron ions (particularly trivalent iron ions), and selectively traps iron ions, so that the amount of iron ions in the system can be effectively reduced. Further, since non-transferrin-bound iron as iron ions is also effectively trapped, non-transferrin-bound iron that is excessive iron in a living body is effectively trapped, and thus adverse effects caused by the excessive iron in a living body can be reduced. Further, after the excessive iron is trapped in a living body, it can be removed from the living body.

Specifically, the method of trapping iron ions, for example, may be any one of a method of introducing the iron chelating agent (or iron chelating agent-containing composition) of the present invention to an iron ion containing composition or a method of introducing the iron ion containing composition to the iron chelating agent of the present invention (or iron chelating agent-containing composition). Further, examples of the iron ion containing composition include liquid phase materials containing iron ions, and aqueous liquid phase materials are preferable. Further, the iron chelating agent-containing composition is suitably determined according to the types used, and is not limited. Examples of the iron chelating agent-containing composition include liquid phase materials in which the iron chelating agent is dissolved or dispersed; solid phase materials having water solubility or water decomposability in which the iron chelating agent is mixed; capsule-form materials having water solubility or water decomposability which contain the iron chelating agent therein; and solid phase materials (filter, or the like) where the iron chelating agent is fixed.

As for the method of trapping iron ions of the present invention, it is preferable to directly trap iron ions using the iron chelating agent of the present invention, but the iron ions may be complexed (chelated) by other chelating agents such as nitrilotriacetic acid (NTA), N-(2-hydroxyethyl)ethylenediamine-N,N',N'-triacetic acid (HEDTA), ethylenediamine-N,N,N',N'-tetraacetic acid (EDTA), and then iron ions in the complex (in the chelate form) may be captured by the iron chelating agent of the present invention, therefore enabling the trapping of the iron ions.

Further, the iron chelating agent of the present invention has low chelating ability with iron (transferrin-bound iron) bonded to transferrin and most of or all the iron ions from the transferrin-bound iron are not captured (substituted). Therefore, in the present invention, when excessive iron is trapped in a living body, it is possible to effectively trap only non-transferrin-bound iron unnecessary for the living body while most of or all the iron ions from transferrin-bound iron required for a living body are not taken, thus the reduction of excessive iron can be effectively achieved in a living body.

Further, the method of trapping iron ions of the present invention can be used in medical applications or in industrial applications.

As shown below in Examples, the present invention is described in detail, but the present invention is not limited to these Examples.

EXAMPLE 1

2N aqueous sodium hydroxide solution was added to a beaker, D,L-serine (manufactured by Tokyo Chemical Industry Co., Ltd.; powder) as it is was added thereto bit by bit at room temperature (about 25° C.) while stirring, followed by stirring for 30 minutes, thereby dissolving serine in aqueous sodium hydroxide solution. Subsequently, water was removed using an evaporator at a temperature of 40 to 50° C. Subsequently, the white residue was added to methanol in a beaker at room temperature (about 25° C.) while stirring, followed by stirring for 30 minutes. Thereby, the resultant was dissolved and salicylaldehyde having the same number of moles as D,L-serine was directly added to this solution at room temperature (about 25° C.) while stirring. At this time, the solution rapidly became a yellow color.

Next, methanol was completely removed with an evaporator at a temperature of 30 to 40° C., and the remaining yellow solid was dissolved in methanol in a beaker at room temperature (about 25° C.) while stirring. Solid state of sodium borohydride ($NaBH_4$) as it is was added bit by bit to the methanol solution at room temperature (about 25° C.) while being stirred. At this time, the solution became white. When all of the yellow components were come out (about 60 minutes), the addition of sodium borohydride was stopped, followed by stirring at room temperature (about 25° C.) for 1 hour, a small amount of water was added at room temperature (about 25° C.), and then insoluble materials were filtered off by natural filtration.

Then, the solvent was removed from the filtrate using an evaporator at a temperature of 40 to 50° C., the remaining white residue was added bit by bit to water in a beaker at room temperature (about 25° C.) while being stirred, followed by dissolution in water. Then, to this aqueous solution was slowly added 2N aqueous hydrochloric acid solution at room temperature (about 25° C.) while being stirred. At this time, white crystals were precipitated according to reduction of pH of the solution (at this time, the pH was 1 or higher).

Then, the resultant was left (still standing) at room temperature (about 25° C.) for one day, the crystals were filtered by suction filtration, washed with methanol and dried using a desiccator for 24 hours to obtain an iron chelating agent (iron chelating agent where serine was used; o-[(1-carboxy-2-hydroxyethyl)-amino-methyl]-phenol) represented by the following formula (3a).

[Chem. 3]

(3a)

EXAMPLE 2

An iron chelating agent (iron chelating agent where histidine was used; o-[(1-carboxy-2-(1H-imidazol-4-yl)ethyl)-amino-methyl]-phenol)) represented by the following formula (3b) was obtained in the same manner as in Example 1.

[Chem. 4]

(3b)

EXAMPLE 3

An iron chelating agent (iron chelating agent where glutamine was used; o-[(1-carboxy-2-carbamoylmethyl-ethyl)-amino-methyl]-phenol) represented by the following formula (3c) was obtained in the same manner as in Example 1.

[Chem. 5]

(3c)

COMPARATIVE EXAMPLE 1

As the iron chelating agent, the free salt of nitrilotriacetic acid (NTA) (trade name "24501-42 (NTA)") and sodium salt (trade name "245-02" (NTA Disodium Salt:NTA2Na) and "24503-22" (NTA Trisodium Salt:NTA3Na) manufactured by Nacalai Tesque) was used.

COMPARATIVE EXAMPLE 2

As the iron chelating agent, citric acid was used. Further, as for evaluation of the iron chelating agent, a commercially available ammonium salt of an iron citrate complex where citric acid was chelated to iron, trade name "F5879-100G" (manufactured by Sigma Corporation; Ammonium iron (III) citrate) was used.

COMPARATIVE EXAMPLE 3

As the iron chelating agent, the sodium salt of N-(2-hydroxyethyl)-ethylenediamine triacetic acid (HEDTA) (trade name "H2378-100G", manufactured by Sigma Corporation; HEDTA trisodium salt hydrate) was used.

[Evaluation A of Iron Chelating Agent]

Evaluation was carried out by the following evaluation method A as to whether the iron chelating agent according to Example 1 had chelating ability with iron.

(Preparation Method of Iron Chelating Agent Solution)

335 mg of the iron chelating agent (MW:209.2) according to Example 1 was added to a 50 mL conical tube, 15 mL of Dulbecco's phosphate buffered saline (pH 7.2;1×D-PBS) was added thereto, 70 mg of sodium hydroxide (MW:40.0) crystal was added thereto, followed by vigorously stirring (shaking) for 10 minutes, and centrifugation (1000 rpm, flashing) was carried out before the lid was opened. Then, 16.75 mL of 1×D-PBS (pH 7.2) was added thereto, and an iron chelating agent solution was prepared having a total amount of 31.75 mL. This iron chelating agent solution ("Fe-Ser•Na(50 mM)") had an iron chelating agent concentration of 50 mM (mmol/L) and a pH of 9.27.

(Preparation Method of Iron Citrate Complex Ammonium Salt Solution)

220 mg of iron citrate complex ammonium salt (trade name "F5879-100G" manufactured by Sigma Corporation; ammonium iron (III) citrate) was taken, 41.5 mL of 1×D-PBS (pH 7.2) was added thereto and dissolved to prepare iron citrate complex ammonium salt solution (dark brown-colored). The iron citrate complex ammonium salt solution ("FAC solution (20 mM)") had an iron ion concentration of 20 mM. Further, 1×D-PBS (pH 7.2) was added to FAC solution (20 mM) to prepare an iron citrate complex ammonium salt solution having a concentration of iron ions of 2 mM ("FAC solution (2 mM)").

(Evaluation Method A)

Iron citrate complex ammonium salt solution [FAC solution (20 mM), FAC solution (2 mM)]", and 1×D-PBS (pH 7.2) were mixed at the ratios shown in Tables 1 to 2, the absorbance of the mixture (wavelength 470 nm) was measured by using a spectrophotometer (trade name "NanoDrop ND-1000 Full-spectrum UV/Vis Spectrophotometer", manufactured by SCRUM Corporation, UV-Vis Module, Measure), and the absorbance of blank ([A] in Tables 1 to 2) was determined. Then, 158 µL of Fe-Ser•Na (50 mM) was added to the mixture, the absorbance (wavelength 470 nm) was measured as described above, and the absorbance after addition of iron chelating agent according to Examples ([B] in Tables 1 to 2) was determined. The results are shown in Tables 1 to 2.

As shown in Tables 1 to 2, it has been concluded that the iron chelating agent according to Example 1 has chelating ability with iron. Particularly, it has been concluded that iron ions can be captured from the iron citrate complex.

TABLE 1

| | | | | | | |
|---|---|---|---|---|---|---|
| FAC solution (20 mM) (µl) | 0 | 10 | 20 | 40 | 80 | 160 |
| 1×D-PBS (µl) | 160 | 150 | 140 | 120 | 80 | 0 |
| 2 µl | ↓ | ↓ | ↓ | ↓ | ↓ | ↓ |
| [A] | 0.000 | 0.005 | 0.009 | 0.015 | 0.029 | 0.057 |
| Fe-Ser•Na (50 mM) (µl) | 158 | 158 | 158 | 158 | 158 | 158 |
| [B] | 0.010 | 0.109 | 0.208 | 0.405 | 0.800 | 1.368 |
| [B]-[A] | 0.010 | 0.104 | 0.199 | 0.390 | 0.771 | 1.311 |

TABLE 2

| | | | | | | |
|---|---|---|---|---|---|---|
| FAC solution (2 mM) (µl) | 0 | 10 | 20 | 40 | 80 | 160 |
| 1×D-PBS (µl) | 160 | 150 | 140 | 120 | 80 | 0 |
| 2 µl | ↓ | ↓ | ↓ | ↓ | ↓ | ↓ |
| [A] | 0.003 | 0.004 | 0.005 | 0.009 | 0.008 | 0.012 |
| Fe-Ser•Na (50 mM) (µl) | 158 | 158 | 158 | 158 | 158 | 158 |
| [B] | 0.015 | 0.027 | 0.040 | 0.055 | 0.104 | 1.181 |
| [B]-[A] | 0.012 | 0.023 | 0.035 | 0.046 | 0.096 | 0.169 |

[Evaluation B of Iron Chelating Agent]

Evaluation was carried out by the following evaluation method B as to whether the iron chelating agent according to Example 1 had chelating ability with iron.

(Preparation Method of Iron Chelating Agent Solution)

An iron chelating agent solution (Fe-Ser•Na (50 mM)) having an iron chelating agent concentration of 50 mM was prepared in the same manner as the preparation method of the iron chelating agent solution in evaluation method A of the iron chelating agent.

(Preparation Method of Iron Nitrilotriacetate Complex Solution)

Ferric chloride-6 hydrate $FeCl_3 \cdot 6H_2O$ (MW270.30) crystals were dissolved in Milli-Q water to prepare an 80 mM solution (A liquid). Meanwhile, 160 mM of nitrilotriacetic acid solution (B liquid) was prepared by dissolving crystals of the free salt of NTA (191.14) in 6N hydrochloric acid. 10 mL of A liquid and 10 mL of B liquid was taken in a beaker, and sodium hydrogen carbonate $NaHCO_3$ crystals were added bit by bit while stirring slowly. When gas generation was suppressed and the solution changed to a dark green color, the addition of $NaHCO_3$ was completed. Finally, iron nitrilotriacetate complex solution "Fe-NTA solution (20 mM)" having an iron ion concentration of 20 mM made up to 40 mL was prepared.

Further, 1×D-PBS (pH 7.2) was added to Fe-NTA solution (20 mM) to prepare an iron nitrilotriacetate complex solution having a concentration of iron ions of 2 mM ("Fe-NTA solution (2 mM)").

(Evaluation Method B)

Iron nitrilotriacetate complex solution [Fe-NTA solution (20 mM), Fe-NTA solution (2 mM)], and 1×D-PBS (pH 7.2) were mixed at the ratios shown in Tables 3 to 4, the absorbance of the mixture (wavelength 470 nm) was measured by using a spectrophotometer (trade name "NanoDrop ND-1000 Full-spectrum UV/Vis Spectrophotometer", manufactured by SCRUM Corporation, UV-Vis Module, Measure), and the absorbance of blank ([A] in Tables 3 to 4) was determined. Then, 158 µl of Fe-Ser•Na (50 mM) was added to the mixture, the absorbance (wavelength 470 nm) was measured as described above, and the absorbance after the addition of the iron chelating agent according to Examples ([B] in Tables 3 to 4) was determined. The results are shown in Tables 3 to 4.

TABLE 3

| Fe-NTA solution (20 mM) (µl) | 0 | 10 | 20 | 40 | 80 | 160 |
|---|---|---|---|---|---|---|
| 1×D-PBS (µl) | 160 | 150 | 140 | 120 | 80 | 0 |
| 2 µl | ↓ | ↓ | ↓ | ↓ | ↓ | ↓ |
| [A] | 0.003 | 0.004 | 0.010 | 0.026 | 0.055 | 0.112 |
| Fe-Ser•Na (50 mM) (µl) | 158 | 158 | 158 | 158 | 158 | 158 |
| [B] | 0.008 | 0.081 | 0.163 | 0.322 | 0.731 | 1.244 |
| [B]−[A] | 0.005 | 0.077 | 0.153 | 0.296 | 0.676 | 1.132 |

TABLE 4

| Fe-NTA solution (2 mM) (µl) | 0 | 10 | 20 | 40 | 80 | 160 |
|---|---|---|---|---|---|---|
| 1×D-PBS (µl) | 160 | 150 | 140 | 120 | 80 | 0 |
| 2 µl | ↓ | ↓ | ↓ | ↓ | ↓ | ↓ |
| [A] | 0.004 | 0.003 | 0.003 | 0.005 | 0.004 | 0.010 |
| Fe-Ser•Na (50 mM) (µl) | 158 | 158 | 158 | 158 | 158 | 158 |
| [B] | 0.011 | 0.017 | 0.026 | 0.041 | 0.075 | 0.135 |
| [B]−[A] | 0.007 | 0.014 | 0.023 | 0.036 | 0.071 | 0.125 |

From Tables 3 to 4, it has been concluded that the iron chelating agent according to Example 1 has chelating ability with iron. Particularly, it has been concluded that iron ions can be captured from an iron nitrilotriacetate complex.

[Evaluation C of Iron Chelating Agent]

Evaluation was carried out by the following evaluation method C as to whether or not the iron chelating agent according to Examples 1 to 3 had chelating ability with iron in 3-morpholinopropanesulfonic acid ($C_7H_{15}NO_4S$;MOPS) and acetonitrile solution as solvents used in high performance liquid chromatography (HPLC).

(Preparation Method of MOPS Solution)

2.09 g of morpholinopropanesulfonic acid ($C_7H_{15}NO_4S$; FW=209.26, Code 341-01801, Lot PX013, manufactured by Dojindo/Wako Corporation) was added to a 100 mL Erlenmeyer flask, 80 mL of ultrapure water (pure water produced by an ultrapure water production system manufactured by Millipore Corporation (Milli-Q); "Milli-Q water") was added thereto and dissolved [pH 4.15 (24.4° C.)]. To this solution, 1N sodium hydroxide solution (1 mol/l sodium hydroxide solution, Code 192-02175, Lot SEP7274, manufactured by Wako Pure Chemicals Industries) was added in 100 µl portions, the pH was adjusted to 7.0 and further Milli-Q water was made up to 100 mL in a measuring cylinder, whereby 100 mL of MOPS solution (pH 6.99) was prepared.

(Preparation Method of Iron Chelating Agent Solution)

An iron chelating agent solution having an iron chelating agent concentration of 50 mM was prepared with respect to the iron chelating agent according to Examples 1 to 3, in the same manner as the preparation method of the iron chelating solution in evaluation A of the iron chelating agent.

Further, 100 mM of MOPS solution (pH6.99) prepared by the preparation method of the MOPS solution was used.

Furthermore, a stock solution of acetonitrile (C2H3N, FW=41.05, Code 347-06641, Lot WPI96, manufactured by Dojindo/Wako corporation) was used.

13.8 mL of Milli-Q water was taken in a 50 mL conical tube, 1.2 mL of each of the iron chelating agent solutions (Fe-Ser•Na (50 mM), Fe-His•Na (50 mM), Fe-Glu•Na (50 mM)) according to the iron chelating agents of Examples 1 to 3 was added, 1.0 mL of 100 mM MOPS solution was added thereto, and a further 4.0 mL of acetonitrile solution was added to produce an iron chelating solution using MOPS. The iron chelating agent solutions using MOPS and iron chelating agent according to Examples 1 to 3 were defined respectively as Fe-Ser•Na (MOPS solution)" (iron chelating agent according to Example 1), "Fe-His•Na (MOPS solution)" (iron chelating agent according to Example 2), and "Fe-Glu•Na(MOPS solution)" (iron chelating agent according to Example 3).

(Preparation Method of Iron Complex Solution)

An iron citrate complex ammonium salt solution (FAC solution (20 mM)) having a concentration of iron ions of 20 mM and an iron citrate complex ammonium salt solution (FAC solution (2 mM)) having a concentration of iron ions of 2 mM were prepared, in the same manner as the preparation method of the iron citrate complex ammonium solution in evaluation A of the iron chelating agent.

Further, iron nitrilotriacetate complex solution ("Fe-NTA solution (20 mM)") having a concentration of iron ions of 20 mM and iron nitrilotriacetate complex solution ("Fe-NTA solution (2 mM)") having a concentration of iron ions of 2 mM were prepared, in the same manner as the preparation method of iron nitrilotriacetate complex solution in evaluation B of the iron chelating agent.

(Evaluation Method C)

FAC solution (20 mM) was added to and mixed with each of the iron chelating agent solutions [Fe-Ser•Na (MOPS solution), Fe-His•Na (MOPS solution), Fe-Glu•Na (MOPS solution)] using MOPS. As a result, the solution became dark brown-colored. Further, FAC solution (2 mM) was added and mixed thereto as described above, and as a result, the solution became dark brown-colored.

Further, Fe-NTA solution (20 mM) was added to and mixed with each of the iron chelating agent solutions [Fe-Ser•Na (MOPS solution), Fe-His•Na (MOPS solution), Fe-Glu•Na (MOPS solution)] using MOPS. As a result, the solution became dark brown-colored. Further, Fe-NTA solution (2 mM) was added and mixed thereto as described above. As a result, the solution became dark brown-colored.

Therefore, it has been concluded that the iron chelating agent according to Examples 1 to 3 has the iron chelating ability even in this solvent system, and that iron ions could be captured from iron citrate complex ammonium salt (FAC) or iron nitrilotriacetate complex (Fe-NTA).

(Evaluation D of Iron Chelating Agent)

Evaluation was carried out by the following evaluation method D with respect to properties whether iron ions were captured from the transferrin iron complex (transferrin iron complex in which transferrin is chelated to iron ions) by the iron chelating agent according to Examples 1 to 2.

(Preparation Method of Iron Chelating Agent Solution)

The iron chelating agent according to Example 1 was dissolved in 1×D-PBS (pH 7.2) to prepare an iron chelating agent solution ("Fe-Ser•Na (5 mM)") having an iron chelating agent concentration of 5 mM, in the same manner as the preparation method of the iron chelating agent in evaluation A of the iron chelating agent.

Further, as described above, the iron chelating agent according to Example 2 was dissolved in 1×D-PBS (pH 7.2) to prepare an iron chelating agent solution ("Fe-His•Na (5 mM)") having an iron chelating agent concentration of 5 mM.

Further, 800 mM HEDTA solution as the iron chelating agent according to Comparative Example 3 was prepared as described above. 13.76 g of crystals were taken in a 50 mL conical tube, 25 mL of Milli-Q water was added and dissolution performed, and then adjustment to pH 7.0 was performed using concentrated hydrochloric acid (35 to 37%) and the total amount was adjusted to 50 mL using Milli-Q water (HEDTA solution (800 mM)). HEDTA solution ("HEDTA solution (5 mM)") having a concentration of HEDTA of 5 mM was prepared using 1×D-PBS (pH 7.2).

(Preparation Method of Nitrilotriacetic Acid Solution)

Further, 800 mM solution (pH 7.0) was prepared by using NTA2Na and NTA3Na as iron chelating agents according to Comparative Example 1 as described above. 9.4 g of NTA2Na was dissolved in Milli-Q water and the total volume was made up to 50 mL (referred to as "NTA2Na solution (800 mM)" in some cases). Meanwhile, 11.0 g of NTA3Na was dissolved in Milli-Q water and the total volume was made up to 50 mL ("NTA3Na solution (800 mM)"). NTA2Na solution (800 mM) (pH 6.3) and NTA3Na solution (800 mM) (pH 11.3) were mixed to produce 800 mM of NTA solution with pH 7.0. NTA solution ("NTA solution (5 mM)") having a concentration of NTA of 5 mM was prepared by using 1×D-PBS (pH 7.2).

(Preparation Method of Transferrin Iron Complex)

A commercially available transferrin iron complex (holo-Transferrin (hTf), human, Code T0665-50MG, Lot 095K1633, manufactured by Sigma Corporation) was dissolved in 1×D-PBS (pH 7.2) to prepare a transferrin iron complex solution having a concentration of iron ions (iron ions which are transferrin-bound iron) of 50 µM.

(Evaluation Method D)

50 µl of 50 µM transferrin iron complex solution was taken in a 1.5 mL sample tube, 50 µl of each of iron chelating agent solutions (Fe-Ser•Na (5 mM), Fe-His•Na (5 mM), NTA solution (5 mM), HEDTA solution (5 mM)) was added thereto and left at room temperature under light shielding for 24 hours. 50 µl of various reaction liquids was taken in a centrifugal ultrafiltration unit (trade name "Amicon Ultra-4 Ultracel-30k" UFC8030, manufactured by Millipore Corporation), and 450 µl of 1×D-PBS (pH 7.2) was added thereto, centrifugation was carried out at 3,500 rpm and 20° C. for 30 minutes, and transferrin and each low molecular chelating agents were separated (first time). After centrifugation, the filtrate was discarded. 450 µl of 1×D-PBS (pH 7.2) was added again to the solution (about 50 µl) containing transferrin concentrated in a unit and centrifugation was carried out with the same conditions (second time). A solution containing transferrin concentrated in a unit was recovered after the second time of centrifugation and the absorbance at the wavelength of 466 nm was measured using a spectrophotometer (trade name "Spectrophotometer DU 640", manufactured by Beckman Coulter). Evaluation results are shown in Table 5.

TABLE 5

| | Holo-Transferrin (hTf) | Chelators | Absorbance (466 nm) | hTf residual ratio (%) |
|---|---|---|---|---|
| Baseline (D-PBS) | (−) | (−) | (−) | |
| Non-treated | (+) | (−) | 0.0740 | 100.00 |
| Example 1 | (+) | Fe-Ser•Na | 0.0772 | 104.32 |
| Example 2 | (+) | Fe-His•Na | 0.0620 | 83.78 |
| Comparative Example 1 | (+) | NTA | 0.0589 | 79.59 |
| Comparative Example 3 | (+) | HEDTA | 0.0515 | 69.59 |

From Table 5, it has been concluded that even when the chelating agent according to Examples was added to the transferrin iron complex solution, there was little change of absorbance (wavelength 466 nm) and all or most of the iron ions were not captured from the transferrin iron complex. Further, in the case of the iron chelating agent according to Example 1, the absorbance (wavelength 466 nm) after the addition to the transferrin iron complex solution was increased. This seems because the iron chelating agent according to Example 1 does not remove iron ions of the transferrin iron complex, but removes background iron ions present in the system.

EXAMPLE 4

The removal of iron in reagents and solvents in the pretreatment of a sample (serum) was attempted by using a chelating agent and ion exchange resin. On the other hand, an ultrafiltration unit was washed using distilled water with iron removed.

Distilled water, PBS:

Distilled water (Wako Pure Chemical Industries) and PBS (Gibco) were subjected to direct addition of 100 g of Chelex (registered mark) 100 Resin (Analytical Grade, 100-200 Mesh, Bio-Rad Labo., hereinafter, referred to as Chelex100) with respect to 3 L of each solution in a reagent bottle, stirred as a whole, and then left to stand before the supernatant thereof was used (batch method).

NTA Solution:

NTA reagents having various lot numbers were prepared, and mixed iron was compared and studied in advance. In addition, the lot number with the least mixed iron was selected. Conventionally, the preparation method of NTA solution includes mixing an NTA•2Na solution (pH 6.30) and an NTA•3Na solution (pH 11.30), and thus the ratio of the mixture was prepared to have the desirable pH. For example, when 0.1 mL of an NTA•3Na solution was added to 5.0 mL of an NTA•2Na solution, the pH of the an NTA solution was 7.21. However, when a strong acidic cation exchange resin is used, it is difficult to adjust the pH of the solution. Also, an NTA solution was prepared with only NTA•3Na, the solution was diluted in MOPS Buffer after the removal of iron, and thus the pH of the NTA solution could be adjusted to a natural range. NTA•3Na crystal (Wako Pure Chemical Industries) was dissolved in distilled water which had been treated with Chelex100 to produce 800 mM of solution (pH 11.42). 1 g of strong acidic cation exchange resin (SK1BH, Mitsubishi Chemical Corporation) was added to 1 mL of 800 mM NTA•3Na solution, and supernatant was recovered after stirring for 1 hour. The solution was diluted ten times in 100 mM MOPS buffer (Dojin Corporation) after completing Chelex100 resin treatment to produce 80 mM NTA•3Na solution (pH 7.08).

[Na$_3$(Co(CO$_3$)$_3$)].3H$_2$O:

This solution is a complex reagent using cobalt•ion as the center, and only iron ions mixed in this solution cannot be removed. When this solution was prepared, the included iron ions were suppressed to the minimum by using a disposable reagent bottle and pipette made of plastic. Chelex100 treatment was carried out in distilled water for dissolving reagents in advance.

Microfiltration Unit:

A suction filter unit used in the preparation of [Na$_3$(Co(CO$_3$)$_3$)].3H$_2$O solution and HPLC mobile phase solution: Stericup-HV (Millipore) was washed twice using 50 mL of distilled water which had been treated with Chelex100 just before use, and iron mixed in the membrane was washed and removed.

Ultrafiltration Filter Unit:

Amicon (registered mark) Ultra-4/Ultracel-30K and Amicon (registered mark) Ultra-0.5/Ultrace10K (Millipore) were washed twice using 0.5 to 1.0 mL of distilled water which had been treated with Chelex100 just before use, and iron contained in the membrane was washed and removed.

Evaluation Method:

Measuring device: Mixed iron ions were evaluated by atomic absorption or a non-metal HPLC system having an OmniSpher5C18 glass•column (G100'3 Rep1), ChromSep guard•column (Varian) equipped on a 2796BioSeparation Module, 2998PhotodiodeArray detector (Waters) using Non-metallic PEEK (polyether-ethylketone) tube.

Distilled Water:

The effect of removing iron by Chelex100 was evaluated using a non-metal HPLC system. As a result, the concentration of iron ions in distilled water after Chelex100 treatment could be suppressed up to the detection limit.

TABLE 6

| Sample name | Peak name | Retention time | Area | % Area | height |
|---|---|---|---|---|---|
| Distilled Water/original | NTBI | 2.749 | 1878 | 100.00 | 158 |
| Distilled Water/Chelex100 | NTBI | none | 0 | 0 | 0 |

PBS:

The effect of removing iron by Chelex100 was evaluated using a non-metal HPLC system. As a result, the concentration of iron ions in PBS after Chelex100 treatment could be observed to be suppressed up to the detection limit.

TABLE 7

| Sample name | Peak name | Retention time | Area | % Area | height |
|---|---|---|---|---|---|
| PBS, original solution | NTBI | 2.799 | 1751 | 100.00 | 121 |
| PBS treated with Chelex100 | NTBI | None | 0 | 0 | 0 |
| d.d. water | NTBI | none | 0 | 0 | 0 |

NTA:

The mixed amount of iron between various lot numbers was compared and studied using a non-metal HPLC system.

TABLE 8

| Reagent: lot | Retention time | Peak area |
|---|---|---|
| NTA•2Na: M0A9187 | 2.706 | 24625 |
| NTA•2Na: B9101026 | 2.712 | 17745 |
| NTA•3Na: M9P9448 | 2.711 | 40657 |
| NTA•3Na: WKP4365 | 2.717 | 26821 |
| Distilled water | none | 0 |

As a result, it was concluded that the reagents had differences in quality depending on the manufacturers thereof. The effect of removing iron was compared and studied using various chelating agents or ion exchange resins.

TABLE 9

| NTA sol | Resin | NTBI (Fe) | Residual ratio | Removal ratio |
|---|---|---|---|---|
| 80 mM NTA•2Na | none | 87.008 µM | 100.00% | |
| | 4002 CL (wet) | 686.407 µM | 788.90% | |
| | SK1BH (wet) | 0.106 µM | 0.12% | 99.88% |
| | CR20 (wet) | 18.649 µM | 21.43% | 78.57% |
| | Chelex 100 (wet) | 51.769 µM | 59.49% | 40.51% |

* Wet: state in which resin is washed with DDW in advance (Chelex treated)

Among four kinds of resins, it was found that SK1BH resin is effective. However, in consideration of the pH of the NTA solution after resin treatment, an NTA solution preparation method was employed.

[Na$_3$(Co(CO$_3$)$_3$)].3H$_2$O:

The concentration of cobalt was measured by ICP mass spectrometry and the concentration of iron was measured by electric heating atomic absorption. In the first preparation, the cobalt and iron concentration of [Na$_3$(Co(CO$_3$)$_3$)].3H$_2$O solution prepared using a reagent bottle made of glass or qualitative filter paper was obtained. An iron content of 0.820 µM was found with respect to 1 mM cobalt concentration. Meanwhile, in the second preparation, in [Na$_3$(Co(CO$_3$)$_3$)].3H$_2$O solution prepared using a reagent bottle and a pipette which are disposable plastic devices, and using a suction filter washed in advance with distilled water which had been treated with Chelex 100 in place of filter paper, the iron concentration could be reduced to 0.014 µM with respect to 1 mM of cobalt. The amount of iron mixed therein could be reduced by 58.5 times between a first preparation and a second preparation.

TABLE 10

| | Test items | |
|---|---|---|
| | Cobalt concentration | Iron concentration |
| First preparation | 0.873 mM | 0.716 µM |
| Second preparation | 12.625 mM | 0.179 µM |

EXAMPLE 5

NTBI in the blood of a healthy person was measured using reagents and solutions after the removal of iron. The measuring method was improved upon the conventional method and a "Subtraction method" was contrived. Iron mixed in NTA reagent scavenging (chelating) non-transferrin-bound iron in serum can be removed, but iron mixed in $[Na_3(Co(CO_3)_3]\cdot 3H_2O$ solution was not completely removed and samples were divided into two components, one was defined as a sample for measuring the total iron concentration with background, the other was defined as a sample for measuring the background iron concentration and the iron concentrations thereof were determined respectively, and a true iron concentration (NTBI) could be calculated by subtracting the background iron concentration from the total concentration. The conventional measuring method is shown below.

Figure 1:
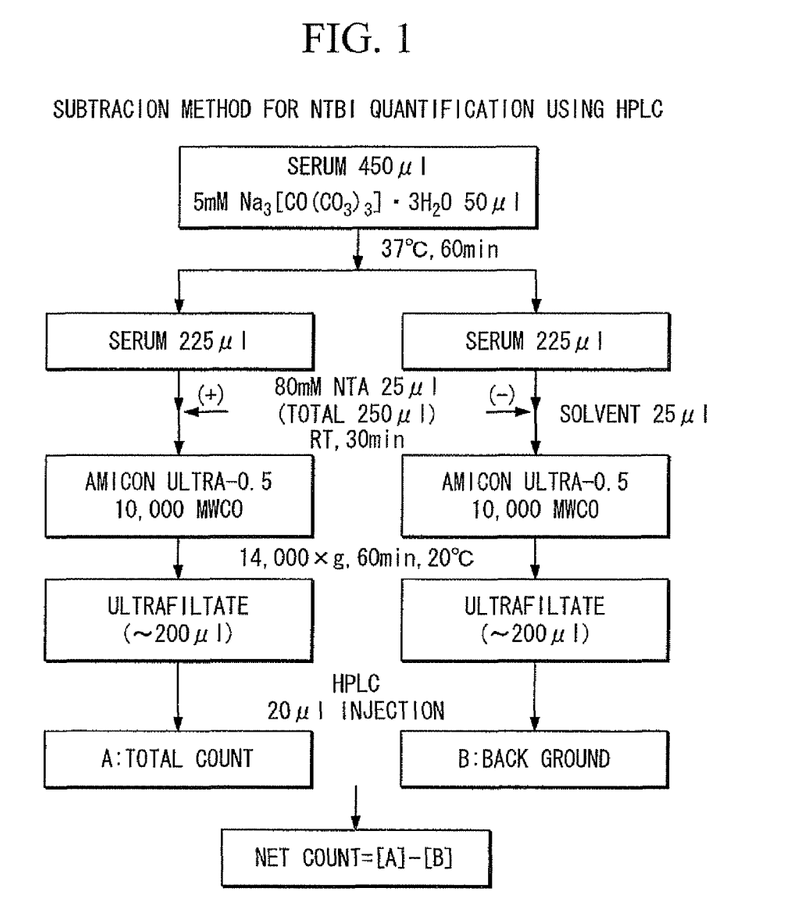
FIG. 1 is an explanatory diagram showing a pretreatment method of samples for measuring iron concentration of the present invention.

Pretreatment of Sample:

A pretreatment method of samples is shown in FIG. 1. Samples (serum) frozen for preservation were thawed rapidly and were refrigerated and stored in ice until used. 450 µl of the thawed sample was taken in a 1.5-mL sample tube, and 50 µl of 5 mM $[Na_3(Co(CO_3)_3]\cdot 3H_2O$ was added thereto. The solution was left in a constant temperature bath at 37° C., and cobalt ions were introduced to the site of iron bound to apotransferrin. After 1 hour, the sample was removed from the constant temperature bath at 37° C., the cobalt ion-treated samples were added in 225 µl portions to two newly prepared 1.5-mL sample-tubes. 25 µl of 80 mM NTA•3Na solution was added to one sample tube (sample A), and 25 µl of solvent used when preparing 80 mM NTA•3Na solution was added to the other sample tube (sample B). The solution was left at room temperature for 30 minutes, and non-transferrin-bound iron (NTBI) was scavenged as Fe-NTA complex. Then, in order that Fe-NTA was separated from iron bonded-protein transferrin, ferritin, or colored protein billirubin in the sample, the sample was added to an ultrafiltration unit with a fractionated molecular weight of 10,000, centrifugation was carried out at 14,000×g at 20° C. for 1 hour, and the ultrafiltrate was recovered. 20 µl of each of the ultrafiltrate of sample A and the ultrafiltrate of sample B was injected to a non-metal HPLC system.

Determination of the Amount of NTBI by HPLC:

Device: A non-metal HPLC system having an OmniSpher5C18 glass•column (G100' 3 Repl), ChromSep guard•column (Varian) equipped on a 2796BioSeparation Module, 2998Photodiode Array detector (Waters) using a Non-metallic PEEK(polyether-ethylketone) tube was constructed.

Mobile phase: 5 mL MOPS (manufactured by Dojin Corporation), 3 mM CP-22 (color chelating agent described in Biochemical Pharmacology 57:1305-1310, 1999; synthesis by requirement), 20% acetonitrile (Wako Pure Chemical Industries) solution was prepared, filtration by a filter unit and degassing were carried out.

Determination of amount: To obtain a standard curve for calculating iron concentrations, Fe-NTA solution in which iron concentration was determined by electrical heating atomic absorbance was used, and a standard curve having iron concentrations in the range of 0 to 10 µM was obtained. 20 µl of each of the ultrafiltrate of sample A and the ultrafiltrate of sample B were injected and an iron concentration was determined from a peak corresponding to a position where Fe-NTA used at the time of determining a standard curve was detected as Fe-CP22 (wavelength in detector was 450 nm), and values obtained by subtracting the iron concentration in sample B (iron concentration as background) from the iron concentration in sample A (the total iron concentration with background) were calculated as NTBI in the sample.

Results:

As a target, healthy persons other than patients having a need for treatment were selected at the time of blood collection. There were two categories which were 20 men (average age 33.4, average Hb value 15.6 g/dl) and 16 women (average age 33.8, average Hb value 13.2 g/dl). The average value of NTBI was 0.206±0.091 µM for the men, and 0.212±0.095 µM for the women.

TABLE 11

| Gender | NTBI (µM) |
|---|---|
| Men | 0.026 ± 0.091 |
| Women | 0.212 ± 0.095 |

With respect to a measuring system using the conventionally reported HPLC, the contamination of iron mixed in at each step was reduced by using various chelating agents and specimens were divided into two portions during the course of measurement and finally subtracting the background, whereby it became possible to measure NTBI at a very low concentration. It was concluded that NTBI was present in the serum of healthy persons by the method established in the present invention, and further measured values also were obtained in a stable manner.

COMPARATIVE EXAMPLE 4

It was thought that the conventional HPLC measuring method has problems due to iron ions in reagents and solutions used in the pretreatment of the samples (serum) shown below. Iron ions are mixed in distilled water as a solvent for dissolving reagents, phosphate buffered saline (PBS) for dilution of the samples, nitrilotriacetic acid (NTA) for trapping NTBI, tris-cobalt carbonate $([Na_3(Co(CO_3)_3]\cdot 3H_2O)$ for blocking the site of iron bonded to apotransferrin. The conventional measuring method is shown in FIG. 2.

Figure 2:
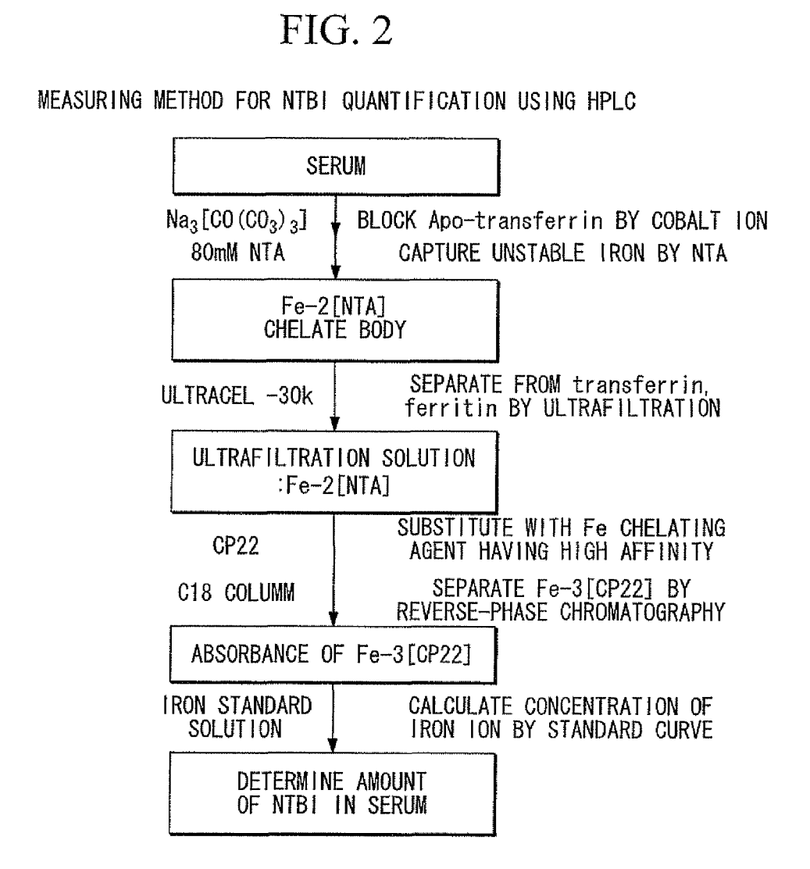
FIG. 2 is an explanatory diagram showing a conventional iron concentration measuring method.

The results of NTBI values in blood measured by the method of FIG. 2 are shown.

TABLE 12

| Sample name | Retention Time | Area | Δ Area |
|---|---|---|---|
| Specimen 1 | 2.829 | 34693 | 13104 |
| Specimen 2 | 2.841 | 19341 | −2248 |
| Specimen 3 | 2.848 | 15902 | −5687 |
| PBS (Background) | 2.855 | 21589 | 0 |

When subtracting the background value in specimens 2 and 3, the results were shown as negative values.

INDUSTRIAL APPLICABILITY

The iron chelating agent of the present invention can selectively chelate with iron ions, in particular effectively chelates non-transferrin-bound iron, and thus it is very useful from an industrial viewpoint.

The invention claimed is:

1. An iron chelating agent, having chelating ability with iron ions, wherein the chelating agent is a compound represented by the following formula (I) or a salt thereof, (1)

wherein Z represents an aromatic hydrocarbon ring or an aromatic heterocyclic ring, $R^1$ in formula (I) is a methylene group, $R^2$ and $R^3$ each independently represent a group having chelating ability, an $R^2$ group having chelating ability in formula (1), which the sum coordination number of groups represented by $R^2$ and $R^3$ is 2, is a carboxyalkyl group, a hydroxyalkyl group, a carbamoylalkyl group, a pyridylalkyl group, a pyrazinylalkyl group, a pyrimidinylalkyl group a pyrrolylalkyl group, an imidazolylalkyl group, a benzoimidazolyalkyl group or a pyrazolylalkyl group, an $R^3$ group having chelating ability in formula (1) is a hydroxymethyl group, a 1-hydroxyethyl group, a (p-hydroxyphenyl)methyl group, an indolylmethyl group, a carbamoylmethyl group, a 2-carbamoylethyl group, a carboxymethyl group, a 2-carboxyethyl group, a 4-aminobutyl group, a (1H-imidazol-4-yl)methyl group, a 3-guanidinoproryl group, a mercaptomethyl group or a 2-methylthioethyl group.

2. The iron chelating agent according to claim 1, wherein ring Z and $R^1$ to $R^3$ in formula (1) do not contain a sulfur atom.

3. The iron chelating agent according to claim 1, wherein the agent is a four or five-coordinated ligand.

4. The iron chelating agent according to claim 1, wherein the agent has chelating ability with respect to non-transferrin-bound iron in a living body.

5. The iron chelating agent according to claim 1, wherein the ring Z in formula (1) is a six-membered aromatic hydrocarbon ring or an aromatic heterocyclic ring.

6. The iron chelating agent according to claim 5, wherein the ring Z in formula (1) is a benzene ring.

7. A method of trapping iron ions comprising contacting the iron ions with the iron chelating agent according to claim 1.

8. The method of trapping iron ions according to claim 7, wherein the iron ions are non-transferrin-bound iron in a living body.

9. A method of producing the iron chelating agent according to claim 1, wherein an aromatic compound or a heterocyclic compound having a structure where a hydroxyl group and a formyl group or a formylalkyl group are bonded to adjacent carbon atoms is reacted with an amino acid or a salt thereof corresponding to an amino acid residue in formula (1).

10. The producing method according to claim 9, wherein the amino acid corresponding to the amino acid residue in formula (1) is serine, threonine, tyrosine, tryptophan, asparagine, glutamine, aspartic acid, glutamic acid, lysine, histidine, or arginine.

11. A method of determining an amount of iron ions by using the iron chelating agent according to claim 1 comprising the steps of:
(a) removing iron from reagents, equipment, and/or solvents,
(b) preparing two samples for which the amount of iron ions is to be determined,
(c) measuring the total concentration of iron and the concentration of iron not originating from the samples, and
(d) subtracting the concentration of iron which is not originating from the samples from the total iron concentration.

12. The method of determining an amount of iron ions according to claim 11, wherein the amount of iron ions is determined by absorption spectrometry.

13. The method of determining an amount of iron ions according to claim 11, wherein the iron ions are non-transferrin-bound iron.

14. The method of determining an amount of iron ions according to claim 11, wherein the step (a) is carried out by the iron chelating agent.

\* \* \* \* \*

UNITED STATES PATENT AND TRADEMARK OFFICE
CERTIFICATE OF CORRECTION

PATENT NO. : 8,623,661 B2  Page 1 of 1
APPLICATION NO. : 13/120126
DATED : January 7, 2014
INVENTOR(S) : Kohgo et al.

It is certified that error appears in the above-identified patent and that said Letters Patent is hereby corrected as shown below:

In the Drawings

Sheet 1 of 2 (FIG. 1) line 1, Change "SUBTRACION" to --SUBTRACTION--.

Sheet 1 of 2 (FIG. 1) line 12, Change "ULTRAFILTATE" to --ULTRAFILTRATE--.

Sheet 1 of 2 (FIG. 1) line 12, Change "ULTRAFILTATE" to --ULTRAFILTRATE--.

In the Specification

Column 3 line 38, Change "$R^2$group" to --$R^2$ group--.

Column 3 line 44, Change "$R^2$group" to --$R^2$ group--.

Column 4 line 57, Change "Advantaegous" to --Advantageous--.

Column 5 line 67, Change "R1" to --$R^1$--.

Column 10 line 10, Change "interadermal," to --intradermal,--.

Column 20 line 62, Change "the an" to --an--.

Column 21 line 8, Change "(Dojin" to --(Dojindo--.

Column 23 line 36, Change "billirubin" to --bilirubin--.

Column 23 line 50, Change "Dojin" to --Dojindo--.

In the Claims

Column 24 line 67, Claim 1, change "(I)" to --(1)--.

Column 25 line 10, Claim 1, change "(I)" to --(1)--.

Column 25 line 18, Claim 1, change "group" to --group,--.

Column 25 lines 19-20, Claim 1, change "benzoimidazolyalkyl" to --benzoimidazolylalkyl--.

Column 25 line 32, Claim 3, change "four or five-coordinated" to --five-coordinated--.

Signed and Sealed this
Twenty-sixth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,623,661 B2  
APPLICATION NO. : 13/120126  
DATED : January 7, 2014  
INVENTOR(S) : Kohgo et al.

Page 1 of 2

It is certified that error appears in the above-identified patent and that said Letters Patent is hereby corrected as shown below:

On the title page, in the illustrative figure, line 1, "SUBTRACION" should
   read --SUBTRACTION--.
On the title page, in the illustrative figure, line 12, "ULTRAFILTATE" should
   read --ULTRAFILTRATE--.
On the title page, in the illustrative figure, line 12, "ULTRAFILTATE" should
   read --ULTRAFILTRATE--.

In the Drawings

Sheet 1 of 2 (FIG. 1) line 1, Change "SUBTRACION" to --SUBTRACTION--.
Sheet 1 of 2 (FIG. 1) line 12, Change "ULTRAFILTATE" to --ULTRAFILTRATE--.
Sheet 1 of 2 (FIG. 1) line 12, Change "ULTRAFILTATE" to --ULTRAFILTRATE--.

In the Specification

Column 3 line 38, Change "$R^2$group" to --$R^2$ group--.
Column 3 line 44, Change "$R^2$group" to --$R^2$ group--.
Column 4 line 57, Change "Advantaegous" to --Advantageous--.
Column 5 line 67, Change "R1" to --$R^1$--.
Column 10 line 10, Change "interadermal," to --intradermal,--.
Column 20 line 62, Change "the an" to --an--.
Column 21 line 8, Change "(Dojin" to --(Dojindo--.

This certificate supersedes the Certificate of Correction issued August 26, 2014.

Signed and Sealed this  
Sixteenth Day of September, 2014

Michelle K. Lee  
*Deputy Director of the United States Patent and Trademark Office*

CERTIFICATE OF CORRECTION (continued)
U.S. Pat. No. 8,623,661 B2

Column 23 line 36, Change "billirubin" to --bilirubin--.

Column 23 line 50, Change "Dojin" to --Dojindo--.

In the Claims

Column 24 line 67, Claim 1, change "(I)" to --(1)--.

Column 25 line 10, Claim 1, change "(I)" to --(1)--.

Column 25 line 18, Claim 1, change "group" to --group,--.

Column 25 lines 19-20, Claim 1, change "benzoimidazolyalkyl" to --benzoimidazolylalkyl--.

Column 25 line 32, Claim 3, change "four or five-coordinated" to --five-coordinated--.